United States Patent [19]

Topp et al.

[11] 4,276,142

[45] Jun. 30, 1981

[54] ELECTROCHEMICAL SENSOR, PARTICULARLY FOR INTERNAL COMBUSTION ENGINE EXHAUST GAS COMPOSITION DETERMINATION, AND METHOD OF ITS MANUFACTURE

[75] Inventors: Bernhard Topp, Gerlingen; Karl-Hermann Friese, Leonberg; Wolf-Dieter Haecker, Asperg, all of Fed. Rep. of Germany

[73] Assignee: Robert Bosch GmbH, Stuttgart, Fed. Rep. of Germany

[21] Appl. No.: 57,253

[22] Filed: Jul. 12, 1979

[30] Foreign Application Priority Data

Jul. 18, 1978 [DE] Fed. Rep. of Germany ....... 2831478

[51] Int. Cl.$^3$ ..................... G01N 27/58; C23C 15/00; B05D 5/12
[52] U.S. Cl. ............................ 204/195 S; 204/192 C; 427/50; 427/124; 427/125
[58] Field of Search ................ 204/195 S, 1 S, 192 C; 422/98; 427/50, 124, 125

[56] References Cited

U.S. PATENT DOCUMENTS

| | | | |
|---|---|---|---|
| 3,645,875 | 2/1972 | Record et al. ..................... | 204/195 S |
| 3,914,169 | 10/1975 | Horowitz ......................... | 204/195 S |
| 3,941,673 | 3/1976 | Takao et al. ...................... | 204/195 S |
| 3,989,614 | 11/1976 | Tien .................................. | 204/195 S |
| 4,080,276 | 3/1978 | Bode ................................. | 204/195 S |
| 4,138,881 | 2/1979 | Isenberg ...................... | 204/195 S X |
| 4,170,530 | 10/1979 | Watanabe et al. ................ | 204/195 S |

FOREIGN PATENT DOCUMENTS

| | | | |
|---|---|---|---|
| 2631721 | 2/1977 | Fed. Rep. of Germany ....... | 204/195 S |
| 52-46515 | 11/1977 | Japan .................................... | 204/195 S |

*Primary Examiner*—G. L. Kaplan
*Attorney, Agent, or Firm*—Frishauf, Holtz, Goodman & Woodward

[57] ABSTRACT

To increase the sensitivity of internal combustion engine exhaust gas sensors, which provide a voltage jump output upon transition of the composition of the exhaust between reducing and oxidizing state, and to maintain the porosity of a platinum, or platinum metal alloy layer forming an electrode on a body of zirconium dioxide, the electrode or electrode layer has dispersed therein an oxide or a carbide of a metal which impedes or inhibits recrystallization at the temperatures to which the sensor is exposed, for example 1000° C., typically zirconium, titanium, tantalum, niobium, aluminum or thorium oxide, or titanium or tantalum carbide, applied, for example, by sequential vaporization of platinum or a platinum metal alloy and the respective metal forming the oxide, in an atmosphere containing residual oxygen, and then oxidizing the remaining metal being applied; or by simultaneous application of a carbide and platinum, for example during simultaneous cathodic atomization, or electron beam vaporization of the respective materials, to form a porous electrode layer of about 2–3 μm thickness, containing approximately 5–40 mol-% of the recrystallization-inhibiting material and having a square resistance not exceeding 20 ohm-square resistance.

21 Claims, 1 Drawing Figure

U.S. Patent   Jun. 30, 1981   4,276,142
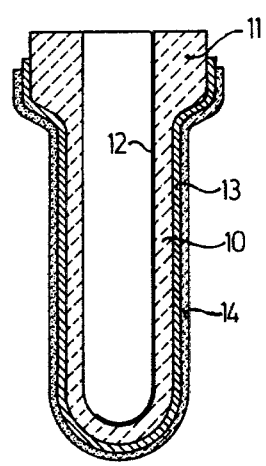

ELECTROCHEMICAL SENSOR, PARTICULARLY FOR INTERNAL COMBUSTION ENGINE EXHAUST GAS COMPOSITION DETERMINATION, AND METHOD OF ITS MANUFACTURE

The present invention relates to an electrochemical sensor, and more particularly to a sensor useful in determination of the oxygen content in the exhaust gases from internal combustion engines, and to a method of its manufacture.

BACKGROUND AND PRIOR ART

Electrochemical sensors to determine whether the exhaust gases from internal combustion engines are reducing or oxidizing are well known and reference is made to U.S. Pat. No. 4,021,326, Pollner et al, which describes a sensor element, and its method of manufacture. The sensor element itself can be secured in a housing or socket for attachment to the exhaust system of an internal combustion engine, for example of an automotive-type engine, in such a way that the sensor element is exposed to the exhaust gases. U.S. Pat. Nos. 3,841,987, Friese et al, and 3,960,692, Weil et al, all assigned to the assignee of the present application, describe complete sensor constructions.

The sensor elements which are usually used, for example as described in the foregoing patents, are shaped in the form of a tube which is closed at one end, made of a solid electrolyte material. The thermodynamic gas balance is provided by an outer electrode which also acts as a catalyst. The electrode, preferably, is made of platinum or a platinum metal alloy. The platinum or platinum metal alloy electrode is in form of a porous layer which is usually applied by thermal vaporizing, vapor deposition, or cathodic atomization. The porous structure should be retained as long as possible in order to achieve a sufficiently high response speed during operation, which thereby increases the useful life of the sensor. To retain the porous structure, it has been proposed to apply a ceramic protective layer over the platinum or platinum metal alloy electrode. If the sensor, with only the porous electrode applied, is treated at an elevated temperature, for example at about 1000° C. for an hour or so, then it will lose about 20% of its response speed. The reason for the drop-off of the response speed apparently is due to recrystallization processes which occur at this temperature, which leads to noticeable disappearance of a portion of the pores. The porous ceramic top cover layer as used heretofore has an inhibiting effect on the recrystallization processes, so that recrystallization is partly prevented. It has been observed, however, that the response speed will gradually drop as the temperature to which the sensor is exposed is increased.

It has previously been proposed to add dispersed metal oxides to metals in order to harden the metals; typically, such additives were made to increase the hardness of copper, gold or platinum, and thus hardened materials were then referred to as having been dispersion-hardened. The purpose of such dispersion hardening is to improve the strength of the metals at elevated temperatures, without substantial change in the other characteristics of the metals themselves. For example, materials which use dispersion-hardened platinum will retain their shape up to approximately the melting point of the platinum itself without otherwise losing physical or chemical properties thereof. The dispersion hardening can be obtained by alloying a few percent—by weight—of a metal oxide to the metal itself.

THE INVENTION

It is an object to provide sensors which have high response speed even though exposed to elevated temperatures so that, effectively, their response speed is stabilized, and to provide methods for rapid and simple manufacturing of such sensors.

Briefly, and in accordance with a feature of the invention, the electrochemical sensor uses a body of solid electrolyte material which has a surface exposed to the gas to be analyzed; that surface has an electrode made of a platinum, or platinum metal alloy applied thereto which catalyzes the gases to establish a stable thermodynamic state thereat. A porous protective layer is applied to the electrode. A second electrode is applied to another surface of the sensor body, the other surface being exposed to a reference gas which, for example, is ambient air. In one form, the sensor is shaped as a closed tube. The electrode which is exposed to the gas to be analyzed contains not only the platinum or platinum metal alloy but additionally has dispersed therein a material which impairs or prevents or inhibits recrystallization of the electrode material at high temperatures. Typically, the inhibiting or impairing material is a metal oxide which is stable at the operating temperature of the sensor, for example an oxide of zirconium, titanium, tantalum, niobium, aluminum or thorium; a stable metal carbide, for example titanium or tantalum carbide, may also be used as the dispersing, recrystallization-impairing material. Preferably, the material is present between 5 to 40 mol-%, and especially between 5 to 35 mol-%.

In accordance with another feature of the invention, the first electrode is applied to the solid electrolyte body by alternately applying the electrode of platinum or a platinum metal alloy and then the metal the oxide of which is to be contained within the electrode, by thermal vaporizing or cathode atomization, the process being carried out in an atmosphere which contains oxygen. In accordance with another feature of the invention, platinum or a platinum metal alloy and a carbide are simultaneously applied to the solid electrolyte body by applying heat by means of an electron beam, or by cathodic atomization.

The sensor which has the dispersed oxides therein has the advantage of high response speed by retaining its porous structure over long periods of operating time. If the solid electrolyte body is made of stabilized zirconium dioxide, then dispersing zirconium dioxide in the platinum layer is particularly advantageous. Alternately applying the metal forming the metal oxide in an oxygen atmosphere, in rapid alternation with the platinum, is a simple and effective process of providing a sensor in which the electrode which is exposed to the gas to be analyzed contains the materials which prevent or at least impair recrystallization of the electrode material.

The structure and method of the present application is not directed to improving the mechanical strength of the electrode material as such, which was the purpose in the dispersion-hardening processes. Rather, the purpose and object of the invention is to improve the response speed of the sensor by maintaining a predetermined microscopic structure (porous) of the thin metal layer forming the electrode on the ceramic carrier body. The content of the additive material to the electrode material as such is higher than that used for dispersion-hardening, that is, in the order of about 5% by weight.

DRAWING

The single FIGURE is a schematic cross section through a sensor element.

A solid electrolyte body, essentially comprising stabilized zirconium dioxide with a wall thickness of 0.5 to 1 mm, is shaped in form of a closed tube 10. The open end of the tube 10 is circumferentially enlarged to form a boss or flange 11. An inner electrode 12 is located at the inside of the tube which, usually, is exposed to ambient air in which the oxygen thereof forms the reference gas. The inner electrode 12 is provided at the inside of the tube, for electrical connection to one sensing or test terminal, as well known. The electrode 12 may, for example, be a conductive track, coating or strip made of a noble metal or of a material which is electron-conductive when an operating temperature has been reached, for example a simple or a compound oxide. The conductive layer may be platinum. The outer surface of the solid electrolyte tube 10 is covered entirely or in part by a layer of platinum, or a platinum-containing metal 13. The layer 13 extends to the flange 11. The thickness of the layer 13 is up to approximately 5 $\mu$m. The platinum layer is coated with a porous, electrically insulating coating 14 of magnesium spinel. The thickness of the magnesium spinel coating is about 50 $\mu$m. The magnesium spinel coating 14 terminates just short of the termination of the platinum layer 13 on the flange 11 to permit attachment of an electrical connection to the layer 13. The coated sensor exhibits a voltage jump when the gas at the outside of the sensor, that is, the surface to which layer 13 and coating 14 are exposed, changes between reducing and oxidizing state.

The sensor is made, as known, by forming the shaped closed tube 10. The tube 10 is then placed in a vapor deposition or evaporating apparatus so that it can be rotatably held therein. The apparatus is so arranged that it has the capability of vaporizing two metals in rapid, alternating sequence. The timing of the alternation can vary between about 1/10 second to several seconds. The atmosphere within the apparatus has a partial oxygen pressure of $10^{-5}$ to $10^{-4}$ mbar. One of the metals is platinum, the other zirconium. The resultant deposit on the body 10 will be an alloy containing zirconium, and zirconium oxide, which is formed by oxidation of the zirconium in the residual oxygen within the evaporating apparatus, the zirconium oxide being dispersed within the platinum. The composition of the alloy can be controlled by suitable choice of the ratio of the evaporating time of the two metals with respect to each other. This relationship can be easily determined empirically. Other metals than zirconium and platinum can be used. The vapor deposition times of the various metals with respect to each other depend on several parameters, such as vapor pressure, specific heat, and similar characteristics.

In accordance with a preferred method, the apparatus is so arranged that the metal to be deposited on the body 10 in form of the electrode, and the metal which forms the oxide for dispersion therein are located within the apparatus so that they can be exposed to a cathode beam, and the cathode beam is controlled, for example by a deflection system similar to that used in television equipment to impinge alternately on the one and on the other metal. This permits control not only of the relative alloying relationship of the metals within the layer which, upon rapid change of the electron beam from one metal container to another, can be considered to be, for all practical purposes, a homogeneous alloy; but additionally, by control of the dwell time of the electron beam on the respective containers or boats for the various metals, the sequence of alloyed or pure metal layer can be controlled so that the layers will grow in respective thickness and sequence; additionally, the number of the layers can be readily controlled. Evaporation of the metals is carried out until the porous layer forming the electrode 13 has a thickness of about 2 to 3 $\mu$m. The time required depends largely on the type of apparatus, and its size, and must be empirically determined.

After vapor deposition, the layer is exposed, in free air, to a temperature of between about 500° C. to 1000° C., for example at about 700° C., which will then convert remaining zirconium to zirconium dioxide. Thereafter, the outer porous layer 14 is applied as a ceramic protective layer; spinel is suitable. It is then only necessary to apply an inner electrode, and the sensor element is ready for assembly into a suitable housing or socket, as well known.

The lower limit of the quantity of the material to be added is that which is necessary to provide sufficient stabilizing effect; the upper limit is about 40 mol-% of a metal oxide or metal carbide. The upper limit is determined by the overall electrical resistance of the layer 13. If too much metal oxide or metal carbide will be present, its resistance will become excessive. The resistance of the layer 13 preferably should not be greater 20 ohm square resistance.

A position controlled electron beam evaporation arrangement is a simple and effective, easily controllable device. Other methods of applying the layer 13 can be used. For example, and in accordance with a feature of the invention, the layer 13 can be made by applying it in two or more independently controlled and independently heated vaporization systems. In a preferred form, electron beam arrangements are used, particularly if a transition metal carbide is to be added to the base electrode material for stabilizing of its structure. Vaporization of transition metal carbide is much more difficult than that of metals which, thereafter, can be converted to oxides.

When using carbides as the additive, concurrent vaporization by concurrently vaporizing platinum and the carbide supply by utilizing two separate electron beam heating systems, to vaporize the respective materials is preferred.

The body 10 can be made in any well-known and suitable manner, for example by pressing, sintering, and then grinding the body to size, and using stabilized zirconium dioxide as a base therefor.

A sensor made by dispersing zirconium dioxide in the porous electrode 13 had these characteristics: zirconium dioxide tube 10
wall thickness: 0.8–1.2 mm.
length: 25–30 mm.
layer 13
  material: pt+zr.
  thickness: ~0.5 $\mu$m; dispersed therein: zirconium dioxide in quantity of: 20 mol-%.
  Protective layer 14: magnesium spinel; thickness: 50–150 $\mu$m.

Various changes and modifications may be made, and features described in connection with any one of the embodiments may be used with the others, within the scope of the inventive concept.

We claim:

1. Method to manufacture a sensor element to sense the composition of gases with respect to a reference gas, comprising
providing a solid electrolyte body (10) having a first surface adapted for exposure to the reference gas;
a first sensing electrode (13) applied to said first surface;
a second surface adapted for exposure to the reference gas, and a second electrode (12) applied to said second surface, and in which the first electrode has dispersed therein a material impeding or inhibiting recrystallization of the material of the first electrode at elevated temperatures,
wherein, in accordance with the invention,
the method of forming and applying the first electrode and the recrystallization-impeding or inhibiting material comprises a plurality of rapidly sequential steps of alternately rapidly vaporizing platinum, or a platinum metal alloy, and a metal which, when oxidized, will form said recrystallization-impeding or inhibiting material, within an atmosphere containing residual oxygen;
and controlling the composition of the electrode layer by controlling the relationship of the vaporization time of the platinum, or platinum metal, with respect to the other metal forming said oxide.

2. Method according to claim 1, wherein the step of vaporizing the platinum, or platinum metal alloy, and said other metal forming the oxide comprises the step of directing an electron beam to impinge, alternately, on said platinum, or platinum metal, and said metal forming the oxide.

3. Method according to claim 1, wherein the step of depositing said platinum, or platinum metal alloy, and the metal forming the oxide comprises cathodic atomization.

4. Method according to claim 1, further including the step of heat-treating the body (10) having said electrode and metal forming the oxide in ambient air to convert residual metal to metal oxide.

5. Method according to claim 4, wherein the heat treatment in air is carried out at a temperature of between 500° C. to 1000° C.

6. Method according to claim 5, wherein the temperature is at about 700° C.

7. Method according to claim 1, wherein the time of alternation between application of, respectively, the platinum, or platinum metal alloy, and the metal, the oxide of which forms said recrystallization-impeding or inhibiting material, is between 1/10 to a few seconds;
and said step of applying the platinum, or platinum metal alloy, and the metal whose oxide forms said recrystallization-impeding or inhibiting material, is carried out until a layer of about 2 to 3 $\mu$m is obtained.

8. Method according to claim 7, wherein the proportion of platinum, or platinum metal alloy, and the metal oxide dispersed therein is sufficient to provide for stabilization of the platinum or platinum metal alloy electrode and sufficiently impeding or inhibiting recrystallization at the elevated temperatures and below a level at which the electrical resistance of the electrode layer is about 20 ohms square resistance.

9. Method according to claim 1, wherein the solid electrolyte body comprises stabilized zirconium dioxide;
the electrode material comprises platinum, and the material which is alternately applied to the body of zirconium dioxide comprises zirconium.

10. Method according to claim 9, further including the step of heat-treating the body (10) having said electrode and metal forming the oxide in ambient air to convert residual metal to metal oxide;
and wherein the relative proportion of application of the platinum and the zirconium is controlled to result in between about 5 to 40 mol-% of zirconium oxide within the electrode.

11. Method according to claim 1, further comprising the step of applying a porous ceramic protective layer (14) over the surface of the body which has said first electrode applied thereto.

12. Method to manufacture a sensor element to sense the composition of gases with respect to a reference gas, comprising
providing a solid electrolyte body (10) having a first surface adapted for exposure to the reference gas;
a first sensing electrode applied to said first surface;
a second surface adapted for exposure to the reference gas, and a second electrode applied to said second surface, and in which the first electrode has dispersed therein a material impeding or inhibiting recrystallization of the material of the first electrode at elevated temperatures,
wherein, in accordance with the invention,
the step of applying said first electrode comprises simultaneously thermally vaporizing and depositing on said surface platinum or a platinum metal alloy and a carbide.

13. Method according to claim 12, wherein said thermal vaporization and depositing step comprises heating platinum and a carbide by electron beam impingement.

14. Method according to claim 12, wherein said thermal vaporization and depositing step comprises heating platinum and a carbide by cathodic atomization.

15. Method according to claim 14, wherein said carbide comprises titanium or tantalum carbide, and the vaporization and application step is controlled to provide between about 5 to 40 mol-% of the metal carbide.

16. Method according to claim 12, further comprising the step of applying a porous ceramic protective layer (14) over the surface of the body which has said first electrode applied thereto.

17. Electrochemical sensor to determine the composition of a test gas comprising
a solid electrolyte body (10) having one surface exposed to the test gas;
a first porous electrode (13) comprising a porous layer of platinum or a platinum metal alloy which catalyzes the test gas to establish a thermodynamic stable state, located on the surface of said body;
a porous protective coating (14) covering said electrode (13);
a second electrode (12) located at another surface of said body, said other surface being exposed to a reference gas;
and a carbide of a metal, which carbide is stable at the operating temperature of the sensor in the presence of the platinum or platinum metal alloy of said first electrode dispersed within the platinum or platinum metal alloy of said first electrode to impede or inhibit recrystallization of the platinum or platinum metal alloy of the first electrode.

18. Sensor according to claim 17, wherein the solid electrolyte body (10) comprises a tube closed at one end of zirconium dioxide, the outer surface of said tube forming said one surface exposed to the test gas and having said first electrode, with the recrystallization-impeding or inhibiting material applied thereto.

19. Sensor according to claim 17, wherein the carbide of the metal is present between 5 mol-% to 40 mol-%.

20. Sensor according to claim 17, wherein said test gas comprises the exhaust gas from an internal combustion engine.

21. Sensor according to claim 17, wherein the recrystallization-impeding or impairing material comprises a material selected from the group consisting of: titanium carbide and tantalum carbide.

* * * * *